United States Patent [19]

Seeburg et al.

[11] Patent Number: 5,075,224

[45] Date of Patent: Dec. 24, 1991

[54] PREPRO-LHRH C-TERMINAL PEPTIDE DNA

[75] Inventors: Peter H. Seeburg, San Francisco, Calif.; John P. Adelman, Eugene, Oreg.

[73] Assignee: Genentech, Inc., South San Francisco, Calif.

[21] Appl. No.: 681,628

[22] Filed: Apr. 2, 1991

Related U.S. Application Data

[60] Continuation of Ser. No. 193,428, May 11, 1988, abandoned, which is a continuation of Ser. No. 84,785, Aug. 13, 1987, abandoned, which is a division of Ser. No. 709,959, Mar. 8, 1985, abandoned, which is a continuation-in-part of Ser. No. 663,097, Oct. 19, 1984, abandoned.

[51] Int. Cl.⁵ ........................ C12P 21/02; C12N 5/10; C12N 15/16

[52] U.S. Cl. ................................ 435/69.4; 435/172.3; 435/240.1; 435/240.2; 435/252.33; 435/320.1; 536/27; 935/13; 935/47; 935/48; 935/69; 935/72; 935/73

[58] Field of Search ................... 435/69.1, 69.4, 172.1, 435/172.3, 240.1, 240.2, 252.3, 252.33, 320.1; 536/27; 935/13, 47, 48, 69, 72, 73

[56] References Cited

U.S. PATENT DOCUMENTS

| | | | |
|---|---|---|---|
| 4,322,499 | 3/1982 | Baxter et al. | 435/320 |
| 4,350,764 | 9/1982 | Baxter et al. | 435/68 |
| 4,366,246 | 12/1982 | Riggs | 435/172.3 |

FOREIGN PATENT DOCUMENTS

| | | |
|---|---|---|
| 0036776 | 1/1981 | European Pat. Off. . |
| 0070186 | 1/1983 | European Pat. Off. . |

OTHER PUBLICATIONS

Barnea et al., Biochem. Biophys. Res. Commun. 67: 1346 (1975).

Charli et al., 7th Int. Cong. Endocrinol. Excerpta Medica, Int. Cong. Series No. 652 Abstract 411 (1984).

Curtis et al., Methods in Enzymology 124: 318–335 (1986).

Curtis et al., Biochem. Biophys. Res. Commun. 117: 872 (1983).

Curtis et al., Endocrinology 112: 390 (1983).

Dhariwal et al., Endocrinology 82: 1236 (1968).

Enjalbert et al., Neuroendocrinology 24: 147 (1977).

Fawcett et al., Endocrinology 96: 1311 (1975).

Furutani et al, Nature 301: 537 (1983).

Gautron et al., Molecular & Cellular Endocrinology 24: 1 (1981).

Greibrokk et al., Biochem. Biophys. Res. Commun. 67: 338 (1975).

Gubler et al., Nature 295: 206 (1982).

Khodr et al., Science 207: 315 (1980).

Jutisz et al., Psychoneuroendocrinology 8: 251 (1983).

Millar et al., "Coll. Int. CNRS" 280, Vincent & Kordon (eds.) CNRS Paris (1977) p. 487.

Millar et al., "Neuropeptides: Biochemical and Physiological Studies", Millar (ed.) Churchill Livingstone, Edinburgh (1981), p. 111.

Millar et al., Biochem. Biophys. Res. Commun. 74: 720 (1977).

Nakanishi et al., Nature 278: 423 (1979).

Nikolics et al., Nature 316: 511 (1985).

Phillips et al., Nature 316: 542 (1985).

Seeburg et al., Nature 311: 666 (1984).

Tan et al., Biochem. Biophys. Res. Commun. 109: 1061 (1982).

Wallace et al., Nucleic Acids Res. 9: 879 (1981).

*Primary Examiner*—Jacqueline Stone

*Assistant Examiner*—Gail Poulos

*Attorney, Agent, or Firm*—Robert H. Benson

[57] ABSTRACT

DNA encoding a novel polypeptide hormone, designated CTP, has been identified in the human genome. CTP is expressed as a fusion protein (proLHRH) with luteinizing hormone releasing hormone (LHRH), and is post-translationally processed to CTP and LHRH. CTP, its derivatives, and its fusions, including proLHRH, are useful in therapy and diagnostics.

11 Claims, 9 Drawing Sheets

Fig. 1.

5' - AGGGCTTTATGTGAGGATTTTTAAAAATTACCATTAAAAAAAAAAAAGCATAGTCCATTTGCAGTATAATTTAC 74

CAGCAGGAAAGATTTCAATGTCCTGGAAAAATTCCCTATAAAAAGGAAGATAGGAAAACAGAAAAGTCACAGTACTCAACCTACTTCAAGGGAAGATTGA 174

GATCTTTTTGGCTCTCTGCCTCTAAACAGGTAAAAGGCTTTGTATTATTTCTAGCACGAGTTTTTCTTCTTTAGATTGCATGCTATTGTATGTCTACAGG 274

GCATTTGACAGCCCAAGGGCTAAATCCAGGTGTGACGGTATCTAATGATGTCCTGTCCTTCACTGTCCTTGCCATCACCAGCCACAGAGATCCAGGCTTT 374

GGGGACTCCCACAGCTTATCGACCAGTGTTTGATTTAGTTTTTAGCCTCTTTCCCATCAAATGAAAATTAACTTGGAGACACATTTCATTAGAAAATTAG 474

AGGCCCCCTTGGCTAGGAAGGCATCTGGTCTGGGACTAACTACTTTGAACAGTGTTGAGTCCTCTCTCCCACAGATGGTTCAGCCAGCAGTAATGCTAGG 574

CAAGACTGAAGGATAAATAGAAAAATGTCATTAGTACCATGGGGTAGCCATGTAATGTCAAGCAATTTTATATTAGCCAGAGATTCCTAGTAGGAGCTAC 674

T

TTTTCTTAACAGATGACTCAGTTCTCTCTATCTCAGGAATGAAAGAGTTGAAGACCAATCCACAACAGGGGAAATGTTAAGGCAAAATGATGAACTTGAT 774

AAGGGATGAATTATGGGGTTTGGATAACCAAACAATAAAAATAAAAGTATAGACTATTTTAGTACTAAAAAGGTCCTGAACATGTGAGCTTAAGTACTCA 874

TTTTGTCCCCAGTGGCTAAGAAACTAAAGGCAAGCCAGCAAGTGTCTCTGAGTTTCAGTGTCTGTATGTAAAAACTGACTCTGACTTCCATCTTCTGCAG 974

C

GGTTAGTGATACAGATGCTAGCTTTTTCACTAAAGAGGTCTTTTAGTTTATACTCAACCTTGTCTGGATCTAATTTGATTGTGCATTCATGTGCCTTAGA 1074

Fig. 1 (Cont.)

```
-23         -20                                   -10                                 -1
met lys pro ile gln lys leu leu ala gly leu ile leu leu thr ser cys val glu gly cys ser ser
ATG AAG CCA ATT CAA AAA CTC CTA GCT GGC CTT ATT CTA CTG ACT TCG TGC GTG GAA GGC TGC TCC AGC      1143

|--------- LHRH ---------|
 1                          10                                      20
gln his trp ser tyr gly leu arg pro gly gly lys arg asp ala glu asn leu ile asp ser phe gln
CAG CAC TGG TCC TAT GGA CTG CGC CCT GGA GGA AAG AGA GAT GCC GAA AAT TTG ATT GAT TCT TTC CAA      1212

                        30                                    40
glu ile val lys glu val gly gln leu ala glu thr gln arg phe glu cys thr thr his gln pro arg
GAG ATA GTC AAA GAG GTT GGT CAA CTG GCA GAA ACC CAA CGC TTC GAA TGC ACC ACG CAC CAG CCA CGT      1281

            50                                    60                                 69
ser pro leu arg asp leu lys gly ala leu glu ser leu ile glu glu glu thr gly gln lys lys ile END
TCT CCC CTC CGA GAC CTG AAA GGA GCT CTG GAA AGT CTG ATT GAA GAG GAA ACT GGG CAG AAG AAG ATT TAA  1353

ATCCATTGGGCCAGAAGGAATGACCATTACTAACATGACTTAAGTATAATTCTGACATTGAAAATTTATAACCCATTAAATACCTGTAAATGGTATGAAT  1453

TTCAGAAATCCTTACACCAAGTTGCACATATTCCATAATAAAGTGCTGTGTTGTGAATG - polyA 3'
```

```
                              A
                              A
                              C
               TC             A
               AG             C
               TC       ─
       A       TC                              A
       A       TC                              A
       A                                       C
       C                                       A
                                               C
5' AAGAGGCAGCACTGGTCTACGGCTTGAGGCCTGGGCGG 3' (+)
   Lys Arg Gln His Trp Ser Tyr Gly Leu Arg Pro Gly Gly  peptide
3' TTCTCCGTCGTGACCAGGATGCCGAACTCCGGACCGCC 5' (−)
                         A
                    AG   G      ─       T
       T            TC          G       ─        ─
       T            AG
       G            TC
       G            AG
       G            TC
       G            AG
       T            TC
       T
```

PREPRO-LHRH C-TERMINAL PEPTIDE DNA

CROSS REFERENCE TO RELATED APPLICATIONS

This is a continuation of application Ser. No. 07/193,428 filed May 11, 1988, now abandoned, which is a continuation of application U.S. Ser. No. 07/084,785 field Aug. 13, 1987, now abandoned, which is a divisional application of U.S. Ser. No. 06/709,959 filed Mar. 8, 1985, now abandoned, which is a continuation-in-part application of U. S. Ser. No. 06/633,097 filed Oct. 19, 1984, now abandoned.

BACKGROUND OF THE INVENTION

This application relates to the identification and synthesis of novel hormones. In particular it is concerned with hormones involved in the biochemistry of reproduction in mammals.

Human reproduction is controlled by the hypothalamic-pituitary-gonadal axis appearing early in fetal development. Luteinizing hormone releasing hormone (LHRH), also termed gonadotropin releasing hormone (GnRH), is a decapeptide of known structure and represents a key molecule in this control circuit. It is produced by hypothalamic neurons, secreted in a pulsatile manner into the capillary plexus of the median eminence and effects the release of luteinizing hormone and follicle stimulating hormone from gonadotrophic cells in the anterior pituitary. LHRH or LHRH-like immunoreactivity has also been found in gonadal tissue placenta, [G. Khodr et al., "Science" 207: 315-317 (1980) and J. Gautron et al., "Mol. Cell. Endocrinology" 24: 1-16 (1981)] and the central nervous system, thereby suggesting additional functions of the peptide. Its presence in the latter, as well as the behavioral effects of exogenously administered LHRH, has led researchers to postulate the involvement of this peptide as a true transcriber in the control of reproductive behavior [R. Moss, "Fed. Proc." 36: 1978-1983 (1977)].

The existence of precursor forms of LHRH were suggested by chromatographic studies of hypothalamic and placental extracts. See J. Gautron, Id., and R. Millar et al., "Biochem. Biophys. Res. Commun." 74: 720-726 (1977). However, these forms were poorly characterized, present in impure mixtures and available only in extremely small quantities.

It has long been recognized that prolactin (PRL) secretion from the anterior pituitary is predominantly under inhibitory control. Although dopamine is known to exert such an inhibitory effect, it has been convincingly demonstrated that dopamine cannot be solely responsible for overall PRL inhibition. The existence of a major PRL-inhibitory factor (PIF) of peptidic nature has been invoked, but such a factor has not yet been characterized from hypothalamic extracts. Attempts to isolate hypothalamic PIF have shown that the areas containing dopamine-free PIF activity were located in the mediobasal hypothalamus and the organum vasculosum lamina terminalis [A. Enjalbert et al., "Neuroendocrinology" 24: 147-161 (1977)], regions which abound in LHRH-producing and secreting neurons. Preliminary purification studies from porcine and ovine hypothalamic tissue allowed size estimates for this activity of between 2000 and 8000 daltons [A. Enjalbert et al., Id.; A.P.S. Dharimal et al., "Endocrinology." 82: 1236-1241 (1968); and T. Greibrokk et al., "Biochem. Biophys. Res. Commun." 59: 704-709 (1974)]. Despite the time that has passed since these publications, the proteins responsible for PIF activity remain uncharacterized and unavailable in pure form.

Accordingly, it is an object of this invention to obtain DNA encoding such LHRH precursors and polypeptides which are coexpressed with LHRH as fusion proteins.

It is another object to identify a polypeptide capable of PIF activity.

It is a further object to synthesize such precursors and polypeptides in recombinant cell culture in large quantities and thereafter to obtain same in purified form.

It is another object to employ such precursors and polypeptides in analytical procedures, in the therapeutic modulation of reproductive cycles and in the treatment of prolactin-dependent tumors.

These and other objects will be apparent to the ordinary artisan from consideration of this specification as a whole.

SUMMARY OF THE INVENTION

DNA encoding an LHRH precursor has been identified in studies of the human genome (FIG. 1). This precursor, preproLHRH, contains in downstream order a eukaryotic signal peptide, LHRH and a C-terminal polypeptide (CTP). The processed fusion of LHRH and CTP is termed proLHRH. ProLHRH is believed to be proteolytically processed in vivo at one, and possibly two, protease cleavage sites, thereby ultimately yielding LHRH and CTP. CTP is defined to include the 53 amino acid polypeptide shown at residues 13 to 66 in FIG. 1. CTP having the additional three carboxy terminal residues Lys Lys Ile is termed GAP (GnRH-associated peptide).

By virtue of the disclosures herein it is now possible to prepare a cell-free polypeptide comprising a CTP amino acid sequence, CTP being defined herein to include CTP as well as mutants or fragments thereof. These cell-free polypeptides include fusions of CTP with eukaryotic proteins such as LHRH (proLHRH) and/or with polypeptides other than the signal polypeptide ordinarily expressed with proLHRH in vivo, e.g. bacterial signals or bacterially secreted proteins. The polypeptides may be administered to mammals in formulations with physiologically acceptable carriers or timed-release agents in order to modulate reproductive cycles or treat PRL-dependent tumors, they may be labelled with detectable markers for use in immunoassays, or they may be employed as immunogens to raise anti-CTP antisera for diagnosis, for purification of CTP or its fusions such as proLHRH, or for derepression of PRL secretion in dairy animals.

DNA encoding these polypeptides is novel, provided (in the case of preproLHRH) that the DNA is obtained free of its natural environment. Thus, DNA which encodes preproLHRH is free of at least one of the two known introns present in the genomic DNA encoding CTP, and cDNA for CTP is free of both introns. Alternatively, the DNA is free of the 5′ or 3′ flanking chromosomal genomic DNA sequences normally found associated with the preproLHRH gene. This DNA is useful in preparing probes for the identification of LHRH-encoding DNA sequences or for transforming hosts to enable the recombinant cell culture synthesis of the various polypeptides described herein.

These polypeptides, including CTP, are synthesized by conventional organic chemical techniques or, preferably, by recombinant DNA methods. The latter comprises transforming a host cell with a vector known to encode the polypeptide followed by culturing the cells and, ordinarily, recovering the polypeptide from the cell.

BRIEF DESCRIPTION OF THE DRAWINGS

FIG. 1 discloses the amino acid and nucleotide sequence of preproLHRH and its cDNA as isolated from human placental tissue. Numbers for amino acids appear within the sequence, whereas nucleotide numbers are given on the right hand side. The nucleotide sequence is that of an approximately 1500 bp cDNA clone (λLHRH-1) isolated as described in Example 2. The cDNA for a shorter cDNA starts at nucleotide 683 (see horizontal arrow). Nucleotide differences between the two cDNAs (positions 702 and 997) are indicated. The overlined ATG indicates an alternative translational initiation codon. The Lys-Arg processing site for the precursor sequence is boxed and the glycine involved in carboxy-terminal amidation is underlined. A second possible processing site at the carboxy-terminus of the prescusor protein is hyphened. Arrows point to interruptions due to introns in the corresponding genomic DNA sequence. The AATAAA polyadenylation signal is underlined.

DETAILED DESCRIPTION

Figure 2:
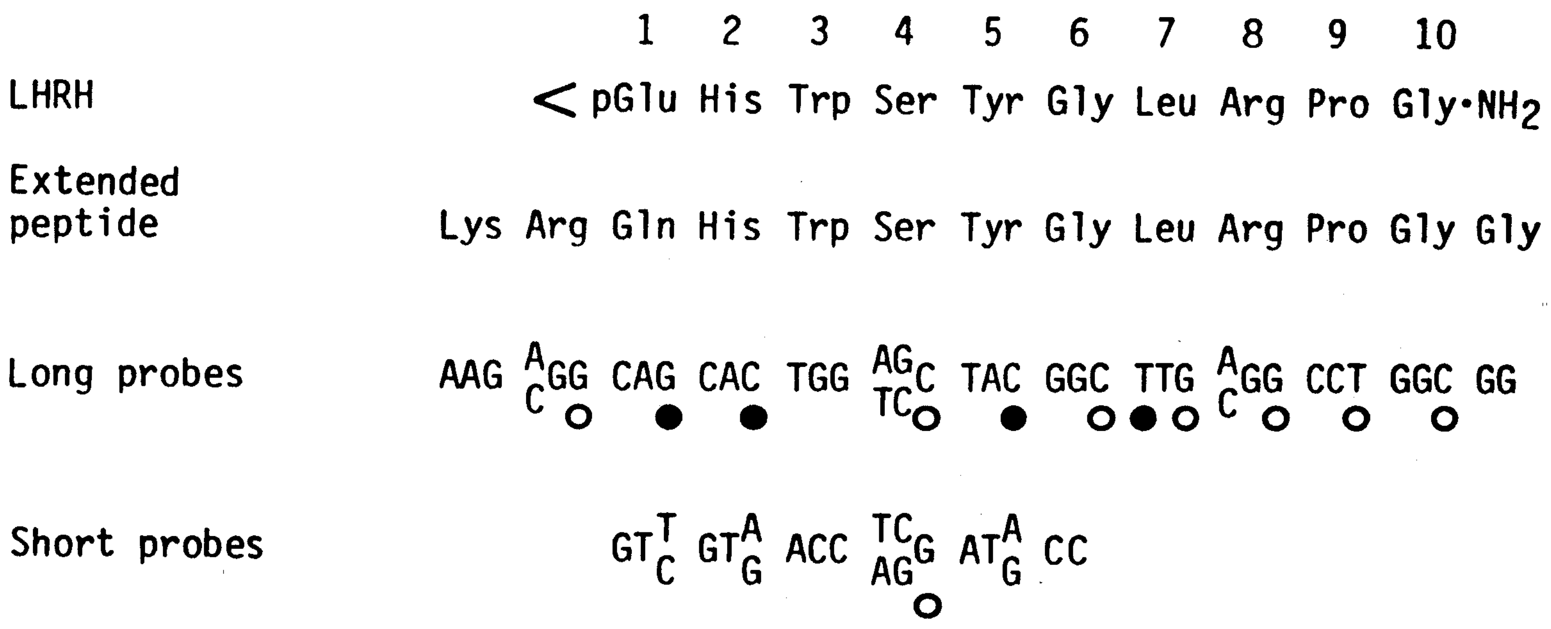
FIG. 2 discloses the chemically synthesized oligonucleotides used in the isolation of LHRH coding sequences. The amino acid sequence of LHRH (1-10) is shown together with what at the time of generating the probes was a conjectural sequence for part of the LHRH precursor ("Extended Peptide"). Based on this sequence a pool of eight oligonucleotides ("long probes", 5' to 3') was designed to be used as probes for the screening of a human genomic library. The single choice of TTG for the Leu codon was based on evolutionary arguments. The pool of sixteen heptadecamers with a sequence complementary to that coding for amino acids 1 to 6 of LHRH ("short probes", 3' to 5') was used to further select between the large number of genomic clones that hybridized with the long probes. Filled circles represent one of two, and open circles one of four possible nucleotides in third codon positions.

CTP is defined herein to include not only the putative 53 amino acid native sequence set forth in FIG. 1 but, for convenience, CTP is also defined to include polypeptides which are CTP fragments or mutations of CTP or such fragments. Polypeptides falling within the scope herein will be immunologically cross-reactive with CTP or will exhibit substantially the same biological activity as CTP. "Substantially the same biological activity" means that the candidate protein retains some but not necessarily all of the CTP biological functions, for example, the ability of CTP to bind to cell-surface receptors.

CTP mutations include deletions, insertions or substitutions of CTP or its fragments. For example, cys at 40 may be substituted by serine in order to improve the oxidative stability of the molecule. The putative lys-lys and lys-arg proteolysis sites at 12-13 and/or 67-68 are eliminated by mutating the encoding DNA so that histidine is expressed instead. In addition, other residues may be mutated to enhance biological activity in patients or to improve intracellular stability in microbial expression hosts. Deletion mutations of CTP are distinguished from CTP fragments in that the amino acid sequences of fragments per se are entirely homologous with the corresponding region of CTP, whereas deletion mutants become homologous only upon the insertion of an intermediate gap.

CTP fragments are principally C or N-terminal deletions. The CTP core fragment cys-thr-thr-his-gln-pro-arg-ser-pro-leu-arg-asp-leu-lys (residues 40-53) has been synthesized by organic rather than recombinant techniques, although it also may be produced in recombinant culture by deletion mutagenesis of the CTP cDNA or by synthesis of a truncated gene. CTP is cross-reactive with rabbit antisera raised against the core fragment of CTP and is therefore useful in CTP immunoassays as further described below. It also exhibits native biological activity, albeit diminished when compared to CTP.

CTP fusions are polypeptides having amino acid sequences including an amino acid sequence that, if excised from the fusion, would meet the foregoing definition of CTP. CTP fusions are exemplified most notably by native proLHRH, a fusion of the LHRH decapeptide at its C-terminus via a gly-lys-arg bridge to CTP having 3 additional C-terminal amino acids. Therefore, in this case CTP as defined herein is fused with a eukaryotic hormone at its N-terminus and with a tripeptide at its C-terminus. Another example of a CTP fusion is preproLHRH, wherein the native eukaryotic signal sequence is fused with proLHRH. This fusion is useful for the secretion of proLHRH. Similarly, bacterial signals such as the *E. coli* STII enterotoxin or alkaline phosphatase leaders may be expressed as N-terminal fusions with CTP or proLHRH with the objective of secreting the mature hormones.

Since CTP is putatively defined in terms of a 53 amino acid polypeptide, the C-terminal lys-lys-ile species (FIG. 1) is to be considered a fusion species, but is included within the scope of the CTP definition.

The CTP described in further detail herein is human CTP. However, like proteins from other sources such as porcine and bovine are included within the definition of CTP.

The polypeptides herein can be manufactured by synthesizing the desired amino acid sequence, but this is commercially impractical at present for longer fragments, i.e., those longer than about 15 residues, or for CTP or its fusions. Preferably, CTP is synthesized in cell culture, ordinarily recombinant cell culture.

For recombinant cell culture, DNA encoding the desired polypeptide or a portion thereof is isolated from genomic or cDNA libraries, as is further described herein, or is synthesized in vitro by known techniques. In vitro synthesis is convenient for short DNA segments, i.e., at the present those having less than about 200 bp. While genomic DNA encoding CTP or its normal fusions found in vivo are isolated from any tissues of the species whose CTP is desired, it is preferred in view of the DNA sequence data now made known herein to obtain mRNA from cells known to secrete LHRH, e.g. placenta or hypothalamus, prepare cDNA by reverse transcription in accord with known procedures, and to identify transformants containing such DNA with probes prepared in light of the FIG. 1 sequence information. The synthetic DNA or cDNA then is tailored as required to encode the desired polypeptide and ligated into cloning vectors, or vice versa. Cloning vectors which are not suitable for later use as expression vectors are used to supply DNA for insertion into expression vectors.

A vector is a replicable DNA construct. Vectors are used herein either to amplify DNA encoding CTP (cloning vectors) and/or to express DNA which encodes the polypeptides (expression vectors). An expression vector is a replicable DNA construct in which a DNA sequence encoding a CTP polypeptide is operably linked to suitable control sequences capable of effecting the expression of the polypeptide in a suitable host. Such control sequences include a transcriptional promoter, an optional operator sequence to control transcription, a sequence encoding suitable mRNA ribosomal binding sites, and sequences which control the termination of transcription and translation.

The term "operably linked" as applied herein to DNA or protein functionalities means that one of the functionalities exerts an influence on the other. For example, DNA for a presequence, also known as a secretory leader or signal, is operably linked to DNA for a polypeptide if it is expressed as a preprotein which enables the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading phase.

Examples of vectors include plasmids, viruses (including phage), and DNA fragments which are integratable into the host genome by recombination. Once a plasmid vector has transformed a suitable host, the vector replicates and functions independently of the host genome, or may, in the case of some viruses and fragments, integrate into the genome itself. In the present specification, "vector" is generic to "plasmid", but plasmids are the most commonly used form of vector at present. However, all other forms of vectors which serve an equivalent function and which are, or become, known in the art are suitable for use herein.

Suitable vectors will contain replicon and control sequences which are derived from species compatible with the intended host cell which is to be transfected and transformed.

Generally, a vector is selected for a given host cell so that it will contain an origin of replication, a promoter and a phenotypic selection gene, for example, a gene encoding proteins conferring antibiotic resistance or supplying an auxotrophic requirement, all of which are recognized by and function in the intended host. *E. coli* is typically transformed using pBR322, a plasmid derived from an *E. coli* species [Bolivar et al., "Gene" 2: 95 (1977)]. pBR322 contains genes for ampicillin and tetracycline resistance and thus provides a convenient means for identifying transformed cells. The well-known and commercially available M13 or $\lambda$ phage vectors are employed to advantage as cloning vectors.

Vectors will contain a promoter operably linked to the CTP DNA which is recognized by the host organism. Promoters most commonly used in recombinant DNA construction in prokaryotes include the $\beta$-lactamase (penicillinase) and lactose promoter systems [Chang et al., "Nature", 275: 615 (1978); Itakura et al., 198: 1056 (1977) and Goeddel et al.. "Nature" 281: 544 (1979)] and a tryptophan (trp) promoter system Goeddel et al., "Nucleic Acids Res." 8: 4057 (1980) and EPO App. Publ. No. 36,776). While these are the most commonly used, other known microbial promoters are suitable. Details concerning their nucleotide sequences have been published, enabling a skilled worker operably to ligate them to DNA encoding CTP in plasmid vectors [Siebenlist et al., "Cell" 20: 269 (1980)]. The preferred vector herein is a pBR322 derivative containing the trp promoter with the Shine-Dalgarno sequence of the trp leader and a portion of the trp LE coding sequence.

Suitable host cells are prokaryotes, yeast or higher eukaryotic cells. Prokaryotes include gram negative or gram positive organisms, for example *E. coli* or *Bacillus* species. Higher eukaryotic cells include established cell lines of mammalian origin as described below. The preferred host cell is *E. coli* ATCC 31446, although other prokaryotes such as *E. coli* $\beta$, *E. coli* X1776 (ATCC 31,537), *E. coli* W3110, pseudomonas species, or *Serratia Marcesans* are suitable.

Transformed host cells are cells which have been transfected with a vector bearing the DNA whose expression is desired and which thereafter express protein from the DNA. Here, the expressed CTP or CTP fusion is located in the host cell cytoplasm or is secreted into either the host's periplasmic space or the culture supernatant, depending upon the host cell and signal which is employed with the CTP-encoding DNA.

Eukaryotic microorganisms, such as yeast cultures, also are transformed with CTP-encoding vectors in order to express the polypeptides herein. *Saccharomyces cerevisiae*, or common baker's yeast is the most commonly used among eukaryotic host microorganisms, although a number of other strains are commonly available. The plasmid YRp7 is suitable for CTP expression in yeast [Stinchcomb et al., "Nature", 282: 39 (1979);

Kingsman et al., "Gene", 7: 141 (1979); Tschemper et al., "Gene", 10: 157 (1980)]. This plasmid already contains the trpl gene which provides a selection marker for a mutant strain of yeast lacking the ability to grow in tryptophan, for example, ATCC No. 44076 or PEP4-1 [Jones, "Genetics", 85: 12 (1977)]. The presence of the trpI lesion as a characteristic of the yeast host cell genome then provides an effective environment for detecting transformants by their ability to grow in the absence of tryptophan.

Suitable promoting sequences for use in yeast vectors include the promoters for metallothionein, 3-phosphoglycerate kinase [Hitzeman et al., "J. Biol. Chem.", 255: 2073 (1980)] or other glycolytic enzymes [Hess et al., "J. Adv. Enzyme Reg.", 7: 149 (1968); and Holland et al., "Biochemistry", 17: 4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Other yeast promoters which are transcriptionally activated or expressed by culture growth conditions are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. Any plasmid vector containing a yeast-compatible promoter, origin of replication and termination sequence is suitable. In constructing suitable yeast expression plasmids, the termination sequences associated with the promoted genes are ligated into the expression vector at a point 3' from the polypeptide coding sequences to provide transcriptional termination followed by polyadenylation of the mRNA.

Cultures of cells derived from multicellular organisms may also be used as hosts. This, however, is not required for CTP expression because CTP is a relatively small protein and does not require extensive processing. However, tissue cell culture is advantageous because such cells are more likely to be compatible with soluble CTP than are bacteria In principal, any such cell culture is workable, whether from vertebrate or invertebrate culture. However, interest has been greatest in vertebrate cells, and propagation of vertebrate cells in culture (tissue culture) has become a routine procedure in recent years [*Tissue Culture,* Academic Press, Kruse and Patterson, editors (1973)]. Examples of such useful host cell lines are VERO and HeLa cells, Chinese hamster ovary (CHO) cell lines, and WI38, BHK, COS-7 and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and most preferably Simian Virus 40 (SV40). The early and late promoters are particularly useful because both are obtained easily from the virus as a fragment which also contains the SV40 viral origin of replication [Fiers et al., "Nature", 273: 113 (1978)]. Smaller or larger SV40 fragments may also be used, provided the approximately 250 bp sequence extending from the Hind III site toward the BgI I site located in the viral origin of replication is included. Further, it is also possible, and often desirable, to utilize human genomic promoter or control sequences normally associated with preproLHRH, provided such control sequences are compatible with the host cell systems.

An origin of replication may be provided either by construction of the vector to include an exogenous origin, such as may be derived from SV40 or other viral (e.9. Polyoma, Adenovirus, VSV, or BPV) source, or may be provided by the host cell chromosomal replication mechanism. If the vector is integrated into the host cell chromosome, the latter is often sufficient.

In selecting a preferred host mammalian cell for transfection by vectors which comprise DNA sequences encoding both a CTP and dihydrofolate reductase (DHFR), it is appropriate to select the host according to the type of DHFR protein employed. If wild type DHFR protein is employed, it is preferable to select a host cell which is deficient in DHFR thus permitting the use of the DHFR coding sequence as a marker for successful transfection in selective medium which lacks hypoxanthine, glycine, and thymidine. An appropriate host cell in this case is the Chinese hamster ovary (CHO) cell line deficient in DHFR activity, prepared and propagated as described by Urlaub and Chasin, "Proc. Natl. Acad. Sci." (USA) 77: 4216 (1980).

On the other hand, if DHFR protein with low binding affinity for methotrexate (MTX) is used as the controlling sequence, it is not necessary to use DHFR resistant cells. Because the mutant DHFR is resistant to MTX, MTX containing media can be used as a means of selection provided that the host cells are themselves MTX sensitive. Most eukaryotic cells which are capable of absorbing MTX appear to be methotrexate sensitive. One such useful cell line is a CHO line, CHO-K1 (ATCC No. CCL 61).

In the preferred embodiment described in the Examples, a vector encoding a fusion of CTP with a bacterial protein (trp LE) is transfected into *E. coli* and the organism cultured. This fusion is not soluble in the cellular cytoplasm and accordingly is deposited as a refractile body within the cells. A refractile body is an insoluble aggregate of the heterologous protein, usually visible under a phase contrast microscope at magnifications as low as 1000 fold. Refractile bodies and methods for their recovery are described in EPO published application No. 114,506, published July 1, 1984. This EPO application also describes techniques for solubilizing the desired polypeptides found in refractile bodies which may be employed with CTP.

The lack of an internal methionine residue in the CTP coding sequence facilitates the use of cyanogen bromide to cleave mature CTP away from the bacterial portion of the fusion. However, other known methods for recovering the mature protein from a fusion, e.g. enzymatic digestions, may be employed for this purpose.

The CTP or CTP fusion may be synthesized in yeast, generally as described above, without refractile body formation. Similarly, a CTP fusion linking a selected bacterial signal sequence directly to the N-terminus of CTP can be secreted as mature CTP, again without formation of refractile bodies.

CTP or CTP fusions are recovered from the cytoplasm, periplasm or culture supernatant of the host cell by methods known per se. The recovery process used will depend upon the nature and location of the CTP or its fusion. Periplasmic protein is recovered by osmotic shock, cytoplasmic protein by cell lysis. Then the protein is separated from other insoluble cellular matter by centrifugation and subsequently purified to the desired degree by procedures which are conventional per se, e.g., ion exchange chromatography., gel filtration, high pressure liquid chromatography, immunoaffinity column purification (using absorption to and acid desorption from immobilized anti-CTP), salting-in or salting-out precipitations, and the like.

The recovered and purified protein then is placed into dosage forms for therapeutic administration or labelled with detectable markers for use in immunoassays. In addition, purified or unpurified CTP or its fragments may be employed as immunogens to raise antibodies to CTP (anti-CTP). Anti-CTP may be immobilized, e.g. by covalent bonding to an insoluble matrix or by absorption to a polyolefin surface, for use in the immunoaffinity purification of CTP or its fusions. Or it may be labelled, e.g. with an enzyme such as horseradish peroxidase or with radioiodine, for use in a sandwich-type immunoassay for the determination of CTP or its fusions. Also, CTP which is free of GnRH epitopes is useful in making immunogens for raising antibodies against predetermined CTP domains. This is enabled by the knowledge, made possible by the disclosures herein, of the amino acid sequence for CTP, and is accomplished by linking CTP fragments to immunogenic substances. This enables highly sensitive sandwich immunoassays for CTP in body fluids since antibodies can be raised against epitopes sufficiently separated that binding of antibody to one CTP epitope will not sterically inhibit the binding of labelled antibody directed against the second epitope.

CTP or its fusions are prepared for therapeutic administration by mixing the protein having the desired degree of purity with physiologically acceptable carrier, i.e., carriers which are nontoxic to recipients at the dosages and concentrations employed. Ordinarily, this will entail combining the CTP or its fusions with buffers, antioxidants, low molecular weight (less than about 10 residues) polypeptides, innocuous proteins, amino acids, carbohydrates including glucose or dextrins, and other stabilizers and excipients. This generally is accomplished in aqueous solution, after which the mixture is passed through a filter having pores sufficiently small to exclude bacteria. The sterile filtrate is filled into vials and desirably lyophilized for long-term storage.

CTP compositions are administered to animals having reproductive dysfunctions or for purposes of modulating reproductive cycles, e.g. menstruation. The route of administration is in accord with known methods, e.g. intravenous, intranasal, intraperitoneal, or intramuscular infusion or injection of sterile solutions, or by timed release systems as noted below.

CTP compositions desirably are administered from an implantable timed-release article. Examples of suitable systems for proteins having the molecular weight of CTP include copolymers of L-glutamic acid and gamma ethyl-L-glutamate [u. Sidman et al., "Biopolymers" 22 (1): 547-556 (1983)], poly (2-hydroxyethyl-methacrylate) [R. Langer et al., "J. Biomed. Mater. Res." 15: 167-277 (1981) and R. Langer, "Chem. Tech." 12: 98-105 (1982)] or ethylene vinyl acetate (R. Langer et al., Id.) Such articles are implanted subcutaneously. Alternatively, CTP is embedded in an adhesive skin patch for slow transcutaneous administration.

The amount of CTP or CTP fusion that is administered will depend, for example, upon the route of administration and the condition of the patient. It will be necessary for the therapist to titer the dosage and modify the route of administration as required to obtain optimal biological activity.

The diagnostic methods used in assaying CTP, its fusions (particularly proLHRH) and antibodies thereto are conventional. These include the competitive, sandwich and steric inhibition techniques. The first two methods employ a phase separation step as an integral part of the method while steric inhibition assays are conducted in a single reaction mixture. The methodology for assay of CTP or its fusions on the one hand and for substances that bind CTP or its fusions on the other are essentially the same, although certain methods will be favored depending upon the size of the substance being assayed. Therefore the substance to be tested is referred to herein as an analyte, irrespective of its status otherwise as an antigen or antibody, and proteins which bind to the analyte are denominated binding partners, whether they be antibodies, cell surface receptors or antigens.

Analytical methods for CTP, its fusions, anti-CTP or CTP cell surface receptors all use one or more of the following reagents: Labelled analyte analogue, immobilized analyte analogue, labelled binding partner, immobilized binding partner and steric conjugates. The labelled reagents also are known as "tracers".

The label used is any detectable functionality which does not interfere with the binding of analyte and its binding partner. Numerous labels are known for use in immunoassay, examples including enzymes such as horseradish peroxidase, radioisotopes such as $^{14}C$ and $^{131}I$, fluorophores such as rare earth chelates or fluorescein, spin labels and the like. Conventional methods are available to covalently bind these labels to proteins or polypeptides. Such bonding methods are suitable for use with CTP, CTP fusions, anti-CTP and CTP receptors, all of which are proteinaceous.

Immobilization of reagents is required for certain assay methods. Immobilization entails separating the binding partner from any analyte which remains free in solution. This conventionally is accomplished by either insolubilizing the binding partner or analyte analogue before the assay procedure, as by adsorption to a water insoluble matrix or surface (Bennich et al., U.S. Pat. No. 3,720,760) or by covalent coupling (for example using glutaraldehyde cross-linking), or by insolubilizing the partner or analogue afterward, e.g., by immunoprecipitation.

Steric conjugates are used in the steric hindrance method for homogeneous assay. These conjugates are synthesized by covalently linking a low molecular weight hapten to a small analyte so that antibody to hapten substantially is unable to bind the conjugate at the same time as anti-analyte. Under this assay procedure the analyte present in the test sample will bind anti-analyte, thereby allowing anti-hapten to bind the conjugate, resulting in a change in the character of the conjugate hapten, e.g., a change in fluorescence when the hapten is a fluorophore. The CTP core fragment described above is suitable for use as the analyte component of the conjugate.

Other assay methods, known as competitive or sandwich assays, are well established and widely used in the commercial diagnostics industry.

Competitive assays rely on the ability of a labelled analogue (the "tracer") to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of CTP, its fusions or anti-CTP present in the test sample. These heterologous assays are called ELISA systems when enzymes are used as the detectable markers.

Another species of competitive assay, homogeneous assay, does not require a phase separation. Here, a conjugate of an enzyme with the analyte is prepared so that when anti-analyte binds to the analyte the presence of the anti-analyte modifies the enzyme activity. In this case, CTP or its immunologically active fragments are conjugated with a bifunctional organic bridge to an enzyme such as peroxidase. Conjugates are selected for use with anti-CTP so that binding of the anti-CTP inhibits or potentiates enzyme activity. This method per se is widely practiced under the name EMIT.

Sandwich assays particularly are useful for the determination of CTP fusions, anti-CTP or CTP cell surface receptors, i.e., large molecules. In sequential sandwich assays an immobilized binding partner is used to adsorb test sample analyte, the test sample is removed as by washing, the bound analyte is used to adsorb labelled binding partner and bound material then separated from residual tracer. The amount of bound tracer is directly proportional to test sample analyte. In "simultaneous" sandwich assays test sample is not separated before adding the labelled binding partner. A sequential sandwich assay using anti-LHRH as one antibody and anti-CTP as the other is useful in testing samples in such a way as to distinguish proLHRH from CTP and LHRH. For example, an excess of anti-LHRH is immobilized on the inner surface of a test tube or microtiter well. This will bind both LHRH and proLHRH from the sample. Then anti-CTP is added. Anti-CTP will be bound in direct proportion to proLHRH because it does not recognize LHRH, or if it does so it will do so with greatly reduced affinity.

The foregoing are merely exemplary assays for CTP, CTP fusions, anti-CTP and CTP cell surface receptors. Other methods now or hereafter developed for the determination of these analytes are included within the scope hereof.

In order to simplify the Examples that follow, certain frequently recurring methods known to those skilled in the art are generally described below; these methods will not be described at each occurrence in the Examples other than by use of the noted key phrases.

Plasmids are designated by a low case p preceded and/or followed by capital letters and/or numbers The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, about 1 μg of plasmid or DNA fragment is used with about 1 unit of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates (dephosphorylation) to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional [T. Maniatis et al., *Molecular Cloning*, pp. 133–134 (1982)].

"Recovery" or "isolation" of a given fragment of DNA from a restriction digest means separation of the digest on polyacrylamide gel electrophoresis, identification of the fragment of interest by comparison of its mobility versus that of marker DNA fragments of known molecular weight, removal of the gel section containing the desired fragment, and separating the gel from DNA. This procedure is known generally. For example, see R. Lawn et al., "Nucleic Acids Res." 9: 6103–6114 (1981), and D. Goeddel et al., "Nucleic Acids Res." 8: 4057 (1980).

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, "J. Mol. Biol." 98: 503–517 (1975), and hybridization as described by T. Maniatis et al., "Cell" 15: 687–701 (1978).

"Transformation" means introducing DNA into an organism so that the DNA is replicable, either as an extrachromosomal element or chromosomal integrant. Unless otherwise provided, the method used herein for transformation of *E. coli* is the $CaCl_2$ method of Mandel et al., "J. Mol. Biol." 53: 154 (1970).

"Ligation" refers to the process of forming phosphodiester bonds between two double stranded nucleic acid fragments (T. Maniatis et al., Id., p. 146) . Unless othrwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id. p. 90., may be used.

"Oligonucleotides" are short length single or double stranded polydeoxynucleotides which are chemically synthesized by known methods and then purified on polyacrylamide gels.

All literature citations are expressly incorporated by reference.

EXAMPLE 1

Isolation of Genomic Sequences Coding for LHRH

A genomic library was used in preference to cDNA libraries to initially screen for LHRH encoding DNA sequences. This choice was dictated by a number of reasons, among which the anticipated low abundance of LHRH mRNA, the possibility of a very long 3' untranslated region, and the unknown location of the decapeptide coding unit within the mRNA figured prominently. The probe strategy employed in the genomic screen is illustrated in FIG. 2. The LHRH decapeptide was extended by three amino acid residues on the assumption that this peptide is preceded in its precursor protein by a processing site in the form of a pair of basic amino acids, that a Gln residue gives rise to the amino-terminal pyro Glu of LHRH, and a Gly residue donates its amino group during carboxy-terminal amidation. This extended peptide sequence was used to design a set of eight chemically synthesized [R. Crea et al., "Nucleic Acids Res." 8: 2331-2348 (1980)] oligonucleotides 38 bases in length ("long probes"). The degeneracy of these probes allowed for the two codon types for Arg (AGPu and CGX) and Ser (AGPy and TCX), but for only one of any two (filled in circles) or four (open circles) choices for all third codon positions. In addition, a set of sixteen heptadecamers ("short probes") which covered all but three of the possible coding sequences for the amino-terminal six amino acids of LHRH was synthesized and would be used below to further select candidates from the clones isolated by the long probes.

Figure 3:
FIG. 3 illustrates the analysis of the synthesized FIG. 2 long probes. The double-stranded DNA shown is composed of the synthetic 38-mer pool (+) coding for the extended LHRH peptide (FIG. 2) and a complementary nonameric primer (both in bold print), together with the rest of the complementary strand (−) generated by enzymatic DNA synthesis (normal print). This DNA was molecularly cloned and fourteen clones were sequence-analyzed. Only nucleotides in degenerate positions are shown above and below the double-stranded DNA. Hyphens denote missing nucleotides. The position of a GMP insertion found in the Tyr codon in one of the cloned DNAs is indicated.
Figure 4A:
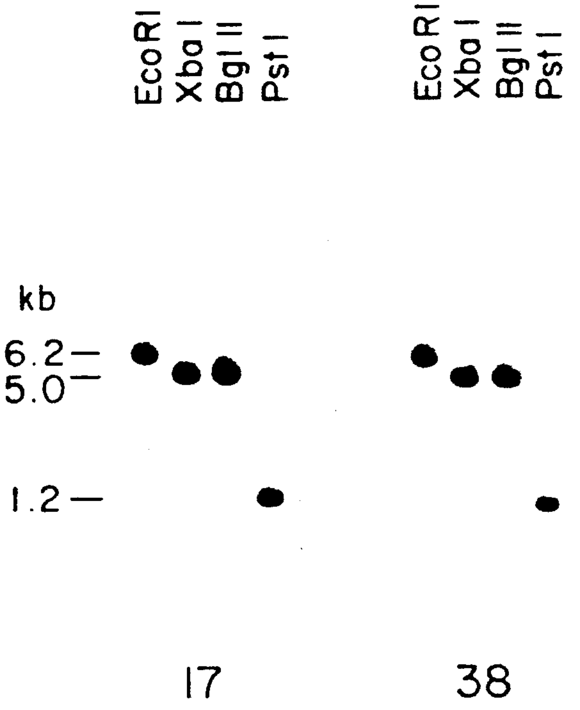
FIG. 4 illustrates the identification of a cloned human genomic DNA segment carrying LHRH coding sequences. Sequential screening of a human genomic library with two pools of oligomers [long (38) and short (17) probes; see FIG. 2] yielded one isolate, the DNA of which hybridized with both oligomeric probes. This is illustrated in panel A, which shows a Southern analysis of the DNA digested with four restriction endonucleases (EcoRI, XbaI, BglII, PstI). DNA fragment sizes in kilobase pairs (kb) are indicated on the left and were assessed using HindIII-cleaved λ DNA (Bethesda Research Laboratories). Panel B shows a sequencing gel (G,A,T,C) across the region of hybridization with both oligomer pools. The amino acid sequence encoded by the nucleotide sequence in this region is indicated.
Figure 4B:
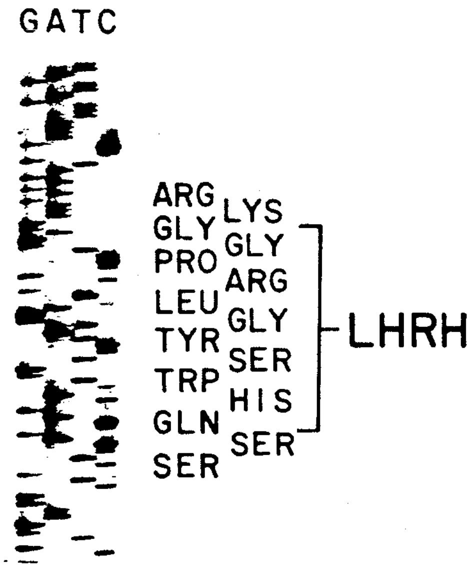
Figure 5:
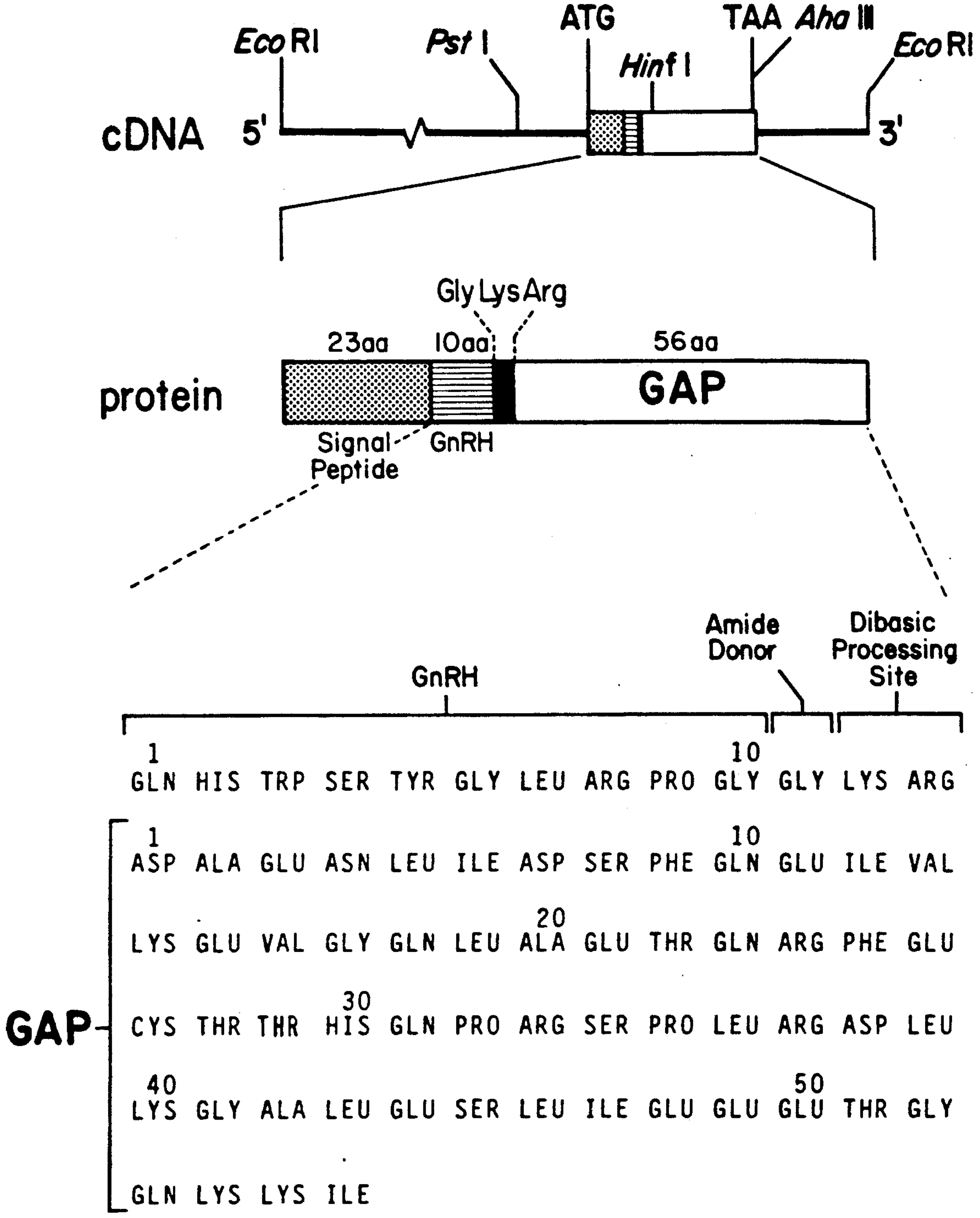
FIG. 5 depicts the restriction enzyme map, structural features and amino acid sequence for the 1500 bp cDNA isolate of FIG. 1. Note that GAP represents CTP-lys-lys-Ile.

Although a similar approach using a single long probe has led to the successful isolation of several genes [S. Anderson et al., "Proc. Natl. Acad. Sci. USA" 80, 6838-6842 (1983); M. Jaye et al., "Nucleic Acids Res." 11, 2325-2335 (1983); A. Ullrich et al., "J. Embo" 3, 361-364 (1984)], the available amino acid sequence in these cases had comprised more than 20 residues. It was clear that success in isolating LHRH coding sequences would rest on the presence of all members of the pool of long probes and on the coincidence by which the correct nucleotide choices were incorporated into a sufficient number of the third codon positions. To analyze pool composition and sequence the oligonucleotides,the oligonucleotide mixture was converted into double-stranded structures using in vitro DNA synthesis in the presence of a chemically synthesized (Crea et al., Id.) nonameric primer molecule (see FIG. 3). 20 pmoles of 5' phosphosylated long probes were annealed with 40 pmoles of 5' phosphorylated nonameric primer in 40 μl of 20 mM Tris.HCl, pH 7.5, 100 mM NaCl, 6 mM $MgCl_2$, 0.1 mM EDTA, 100 μM each of dATP, dGTP, dCTP, dTTP, at 14° C. for 15 min. DNA synthesis was initiated by the addition of 5 U E. coli DNA polymerase I (large fragment, Boehringer Mannheim) and allowed to proceed for 30 min at 14 C. Following phenol extraction and ethanol precipitation the DNA was incubated for 2 hrs at room temperature with 10 ng SmaI-cleaved M13 mp10 RF-DNA in 20 μl containing 50 mM Tris.HCl, pH 8, 10 mM $MgCl_2$, 0.1 mM EDTA, 10 mM β-mercaptoethanol, 0.5 mM rATP and T4 DNA ligase (New England Biolabs). The ligation mixture was used to transform competent *E. coli* JM103 cells. Recombinant phage was grown, and single-stranded phage DNA prepared and sequenced using dideoxynucleoside triphosphates. FIG. 4 shows the results obtained from analyzing 14 isolates and demonstrates that, most importantly, all the nucleotide combinations of the long probes were represented. Thus, in spite of several deletions predominantly within the Tyr codon and a single nucleotide insertion in the same codon, the quality of the oligonucleotide mixture was considered satisfactory for screening the genomic library.

$10^6$ λ phage containing human genomic DNA [R. Lawn, et al., "Cell" 15: 1157-1163 (1978)] were screened on duplicate filters using the long probes (see FIG. 2) which had been phosphorylated to a specific activity of $10^7$ cpm per pmole. Hybridization was at 37° C. in the presence of 30 percent formamide using $10^7$ cpm per filter. Filters were washed in 3×SSC (1× SSC=0.15 M NaCl, 0.015 M Na-citrate) at 37° C. and exposed to X-ray film. Phage from 300 small areas corresponding to the number and location of positive signals were replated on individual plates and probed with long and short probes (FIG. 2). Short probe hybridization was at room temperature in the presence of 20 percent formamide and corresponding filters were washed at the same termperature in 5× SSC. DNA from the single isolate which hybridized with both pools of oligomers was cleaved with restriction enzymes and DNA fragments were characterized by Southern analysis using the two oligonucleotide pools as probes under the conditions specified above. A 1200 base pair DNA fragment containing the hybridizing region was cloned into phage M13 mp18 RF-DNA and recombinant single-stranded DNA was sequenced using primed DNA synthesis in the presence of dideoxynucleoside triphosphates. The analysis of this clone is shown in FIG. 4. In panel A the same single restriction fragments are seen to hybridize with both sets of oligomers. A sequencing gel showing the hybridizing region is presented in panel B. The amino acid sequence derived from the nucleotide sequence shows that this DNA indeed codes for the LHRH peptide. The DNA sequence also predicted the expected carboxy-terminal Gly residue necessary for amidation followed by a Lys-Arg processing site. Although such a processing site had been expected to, but does not, precede LHRH (see FIG. 2), and although long probes also differed in five nucleotides from the actual LHRH coding region (cf. FIGS. 2 and 1), the sequence homology of these probes was sufficient to identify the correct gene. Because of the possible presence of introns in the gene an effort was made to isolate the corresponding cDNA for elucidating the complete structure of the LHRH precursor protein.

EXAMPLE 2

Isolation of prepro LHRH cDNA

Polyadenylated RNA (10 μg) from human placental tissue was converted into double-stranded cDNA following standard procedures [T. Maniatis, et al., "Molecular Cloning, Cold Spring Harbor Laboratory" (1982)]. The cDNA was cloned using phage λgt10 as a vector according to published methods [T. Huynh, et al., "Practical Approaches in Biochemistry" (1984)]. $1.5\times10^6$ recombinant phage were obtained and screened using a 600 bp Sau3A digestion fragment isolated from the genomic clone and labelled [J. Taylor, et al., "Biochem. Biophys. Acta" 4: 324-330 (1976)] to a specific activity of $10^8$ cpm per μg. Two hybridizing λ clones were isolated and found to contain cDNA inserts of approximately 1500 and 800 base pairs, respectively. These cloned cDNAs were sequenced using single-stranded recombinant M13 DNA as templates for the primed DNA synthesis in the presence of dideoxynucleoside triphosphates. FIG. 1 shows the complete nucleotide sequences of both cDNAs, together with the deduced amino acid sequence of the LHRH precursor protein (preproLHRH).

The most prominent feature of the cDNA is a very long 5'-untranslated region in excess of 1,000 nucleotides. A similarly sized 5' region has been described for the human preproenkephalin B gene but seems otherwise a rare phenomenon. Since LHRH is expressed in various tissues, transcription of the precursor gene from different tissue-specific promoters might be invoked to account for the presence of such an extended 5' region in the placental cDNA. The trivial explanation that the clone is derived from an unspliced nuclear RNA can be refuted since two introns present in the gene had been clearly removed. The smaller of the two cloned cDNAs still features approximately 400 nucleotides of 5'-untranslated sequence which also happen to contain the best consensus splice acceptor site (nucleotides 960-974), thus rendering unlikely the possibility of a partially spliced version. The very low abundance of the corresponding mRNA in placental tissue has so far precluded the use of Northern analysis [H. Lehrach, et al., "Biochemistry (Wash.)" 16: 4743-4751 (1977)] to establish the correct length of its 5' region. Finally, complete colinearity of this region with the established genomic sequence rules out artifacts which might have been introduced during reverse transcription and molecular cloning.

The largest open reading frame (nucleotides 1063-1350) specifies the coding sequence for LHRH and translates into a protein of approximately 10,000 daltons which bears the hallmarks of a precursor for a polyfunctional protein. This reading frame is terminated by an ochre stop codon and followed by 160 nucleotides of 3-untranslated region containing an AATAAA sequence for polyadenylation shortly upstream of the polyA tail. The actual start of translation within the open reading frame is unclear. The first ATG initiation codon (position 1063) is followed by an in-frame ATG four codons downstream. This second ATG, but not the first, is followed by a purine and preceded by an A at position -3, as is the case with most eukaryotic initiation codons. It is concluded that this ATG at position 1075 initiates the synthesis of the LHRH precursor protein even though it involves a violation of the rule which specifies that the first ATG should bear this function [M. Kozak, "Nucleic Acids Res." 9: 5233-5252 (1981)]. It is possible that both ATGs are involved in the initiation of protein synthesis, resulting in a low translational efficiency.

The first 23 amino acids form a typical signal sequence containing a hydrophobic middle section. The putative signal sequence ends in two serine residues followed by the expected decapeptide sequence for LHRH. Cleavage of the signal peptide results in an amino-terminal glutamine residue which spontaneously or enzymatically undergoes cyclization to pyro Glu, the modified amino-terminus of LHRH. The decapeptide sequence is followed by a glycine, the standard donor of the amino group for carboxy-terminal amidation. A Lys-Arg cleavage site is present for enzymatic processing as found in many precursors to neuroendocrine peptides [J. Douglass, et al., "Ann. Rev. Biochem." 53: 665-715(1984)]. Thus, the isolated cDNAs code for a true precursor protein to LHRH which features a direct linkage of signal sequence to biologically active peptide reminiscent of the situation encountered in the precursor for vasopressin [H. Land, et al., "Nature" 295: 299-303 (1982)].

The remainder of the LHRH precursor consists of a peptide of 56 amino acid residues. It does not contain any sites for N-glycosylation (Asn-X-Thr/Ser) and no homologies could be detected when compared to other known hypothalamically produced precursors to neuroendocrine peptides. Interestingly, the carboxy-terminus of this peptide consists of the sequence Lys-LysIle, which is believed to represent an enzymatic cleavage site for further processing. The resulting peptide of 53 amino acids, CTP, (rather than GAP) is believed to be released along with LHRH.

EXAMPLE 3

Construction of Plasmid Encoding a GAP Fusion

Figure 6:
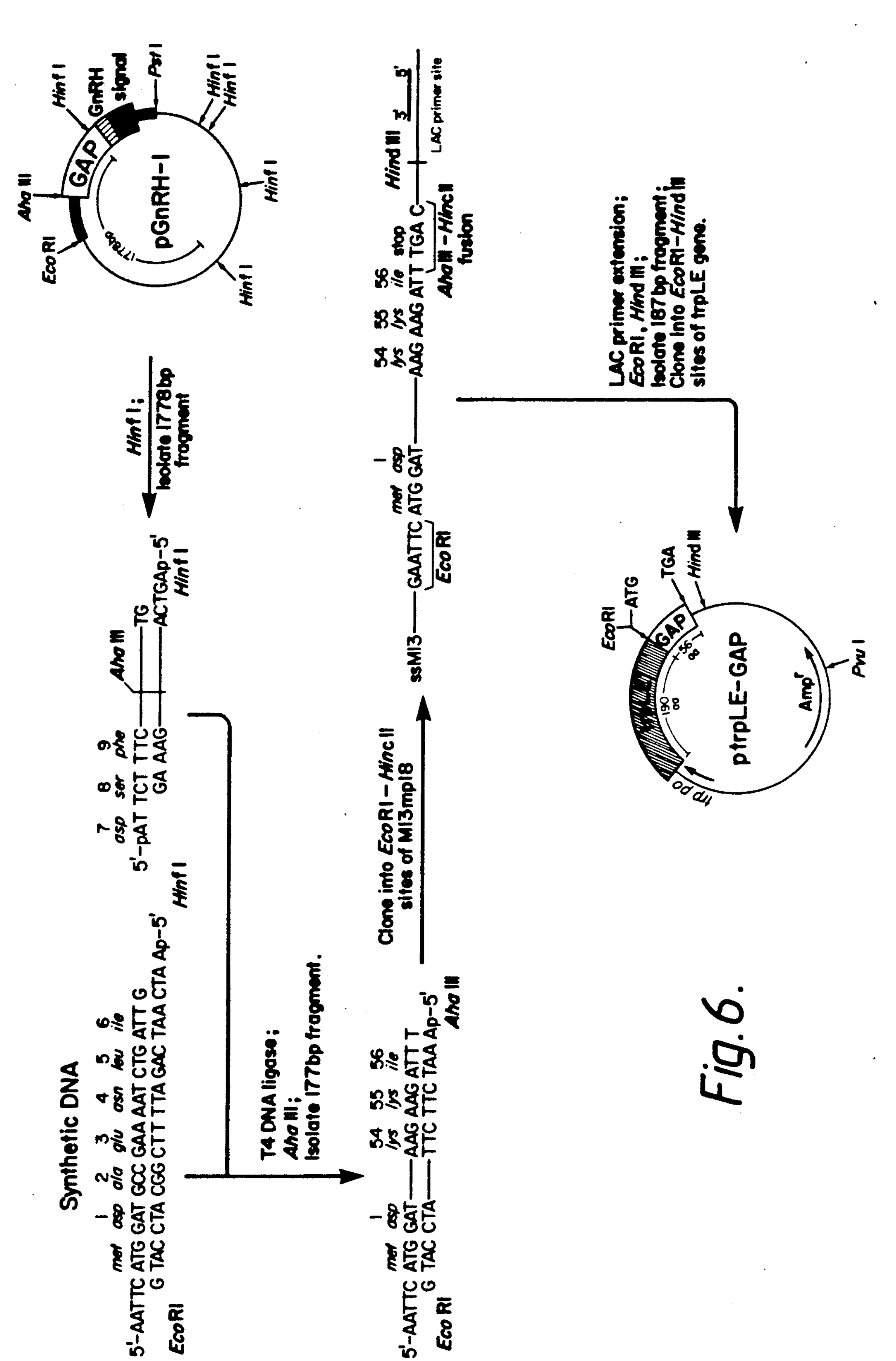
FIG. 6 discloses the preparation of an expression vector for GAP.

The cloned 1500 bp cDNA EcoRI fragment from Example 2 (λ LHRH-1) was subcloned into M13mp19. DNA from this M13 clone was used to isolate the 562 bp EcoRI-PstI fragment in the following way. The single strand M13 template was made double stranded (as required for restriction enzyme cleavage) by priming the DNA with the M13 17-mer universal sequencing primer in the presence of the four dNTP's and the Klenow fragment of DNA polymerase I. Double stranded DNA was digested with EcoRI and PstI and the 562 bp fragment was recovered by polyacrylamide gel electrophoresis and electroelution. This fragment was ligated to pUC 11 which had been digested with PstI and EcoRI, *E. coli* JM83 transformed with the ligation mixture and a plasmid pGnRH-1 (FIG. 6) was recovered from one of the colonies.

pGnRH-1 contains five sites recognized by HinfI. Thus, when pGnRH-1 is digested with HinfI, five fragments are produced. The largest of these, the 1778 bp HinfI fragment, was isolated and this fragment ligated to a synthetic oligonucleotide (FIG. 6) encoding the 5' end of met-GAP sequence. The oligonucleotide is synthesized with a sticky end that only binds to the HinfI sticky end (GATTC) found in the GAP coding region; the other HinfI site contains the sequence GACTC which is not self complementary to the HinfI sticky end in the synthetic DNA. This oligonucleotide was made by synthesizing the two strands, phosphosylating chain 11 (the lower strand in FIG. 6) with polynucleotide kinase, and annealing the two strands together. The ligation product was then digested with AhaIII (forming a blunt end) and the 177 bp AhaIII - EcoRI fragment (encoding GAP fused to the C-terminal tripeptide) recovered.

The 177 bp fragment was ligated to the M13 phage mp18 which had been digested with EcoRI and HincI (forming a blunt end and an EcoRI sticky end). *E. coli* JM101 was transformed with the ligation mixtures and the phage mp18GAP-1 (not shown) isolated from a white plaque. The sequence of the 177 bp fragment was confirmed on ss M13 template by dideoxy sequencing. Single-stranded mp18-GAP DNA was made double-stranded in vitro by elongating the 17-mer LAC primer (J. Messing et al., 1981, "Nucl. Acids. Res." 9: 309-321) in the presence of dNTPs and Klenow. mp18GAP-1 DNA was digested with EcoRI and Hind III, and the 187bp fragment isolated.

ptrpLE, (not shown) a modification of pNCV [Davis et al., "P.N.A.S." 78: 5376 (1981)], lacking tetracycline resistance and including ampicillin resistance and a polylinker region derived from M13 mp18, was digested with EcoRI and Hind III. The digested plasmid DNA was ligated to the 187bp EcoRI-Hind III fragment, the ligation used to transform *E. coli* 294 cells (ATCC 31446) and transformants were identified by Southern analysis using the 562 bp PstI-EcoRI CTP fragment which had been $^{32}P$ labelled ptrpLE-GAP was recovered from a transformant colony.

A similar vector encoding CTP was made by in vitro mutagenesis of the GAP lys 54 codon of mp18GAP-1 to a stop codon. The GAP fusion was more stable to cytoplasmic *E. coli* proteases than CTP.

EXAMPLE 4

Preparation of Anti-CTP

The CTP core fragment $NH_2$-cys-thr-thr-his-gln-pro-arg-ser-pro-leu-arg-asp-leu-lys-COOH, was synthesized. This fragment then was covalently linked to bovine serum albumin (BSA) by crosslinking through cys401 with suberic acid bis (N-hydroxy-succinimide ester) using known techniques. Three rabbits were immunized with the BSA conjugate. All three developed polyclonal antibodies to the fragment, although in varying titers. Serum was harvested from an immunized rabbit and radioiodinated with 131I using the chloramine T procedure. This labelled antiserum was used to monitor the purification of the CTP fusion expressed and purified in Example 5, but would be suitable for assay of CTP or its fusions in clinical test samples such as serum.

EXAMPLE 5

Expression and Recovery of a GAP Fusion

*E. coli* 294 (ATCC 31446) cells were transformed with ptrpLE-GAP. Transformants were inoculated into ½ liter of M9 culture medium containing 50 mg/ml ampicillin and grown to a cell density of about 3 $OD_{550}$. Cells were separated from the stationary phase culture medium and refractile bodies recovered by lysis in 2 percent SDS and 1 percent beta-mercaptoethanol and precipitated with 10 vols. of cold acetone. High density culture used *E. coli* strain K12 W3110 cells. Pelleted refractile bodies were homogenized in 20 ml of 6M guanidine hydrochloride in order to solubilize the protein. The soluble proteins were dialyzed into 4M urea and applied to a Vydac C4, 300 Å,15–20 μm, 5×35 cm column (a silica hydrophobic affinity column) and separated on reverse phase HPLC at a flow rate of 15 ml/min. using a gradient of 25–60 percent acetonitrile/0.1 percent trifluoroacetic acid. 15 ml fractions were collected. Anti-CTP reactive material eluted at about 49 percent vol/vol acetonitrile.

Anti-CTP reactive fractions were lyophilized and then cleaved by cyanogen bromide (CNBr) in known manner: About 5.9 mg of protein was dissolved in 480 μl of 70 percent formic acid. 41.9 μl of CNBr solution (100 mg/ml in formic acid) and 18.8 μl $NaS_2O_3$ solution (10 mg/ml in formic acid) were added to the dissolved protein and the reaction mixture was incubated for 24 hours while shaking. The reaction mixture was diluted into 0.1 percent TFA and chromatographed on a Vydac C18, 300 Å, 15–20 μm, 2.5×35 cm column (a C18 silica hydrophobic affinity column) and eluted with a 30–50 percent acetonitrile/0.1 percent TFA gradient. The fractions containing immunoreactive material were pooled and lyophilized.

This material was dissolved in 2M acetic acid and gel filtered on a Sephadex G-50 column, eluting with 2M acetic acid. Immunoreactive material from the eluate was purified on reverse phase HPLC using a Vydac C4, 300 Å, 5 μm, 1×25 cm column (a C-4 hydrophobic affinity resin) using a 33–45 percent acetonetrile/0.1 percent TPA gradient elution. The 40 percent vol/vol acetonitrile eluate contained a single protein peak and was judged to be homogeneous. The product was confirmed to be GAP by amino acid sequencing and analysis.

EXAMPLE 6

Biological Activity of GAP

Pituitary cells from female Sprague-Dawley rats were established in cell culture by the method of K. Nikolics et al., "Peptides" 2: 65–73 (1981). 1 ml of about $1\times10^{-8}$ molar concentration of GAP or LHRH in medium 199 (a nutrient medium) was added to a four day pituitary cell culture per $5\times10^5$ cells. After 4 hours incubation at 37° C. in 5 percent $CO_2$/95 percent air the cell culture supernatant fluids were assayed for release of LH and FSH. The results are shown in the Table below.

TABLE 1

| Test Sample | LH (pg)/5 × $10^5$ cells | FSH (pg)/5 × $10^5$ cells |
|---|---|---|
| Basal | 4293 ± 474 | 2701 ± 718 |
| LHRH $10^{-8}$M | 30503 ± 3342 | 11403 ± 350 |
| GAP $10^{-8}$M | 25825 ± 2655 | 10496 ± 838 |

From this data GAP is shown to be active in stimulating pituitary cells to release LH and FSH, and accordingly to be useful as an alternative to LHRH in the modulation of reproductive cycles. In a similar experiment the CTP-core polypeptide of Example 4 also was active in LH and FSH release, albeit at higher concentrations than required for GAP.

EXAMPLE 7

Prolactin Release-Inhibiting and Gonadotropin Releasing Action of GAP

To further investigate the prolactin inhibiting and gonadetropin releasing action of GAP, concentration-response relationships were determined and combined applications with factors known to influence the secretion of these anterior pituitary hormones were conducted.

Figure 7A:
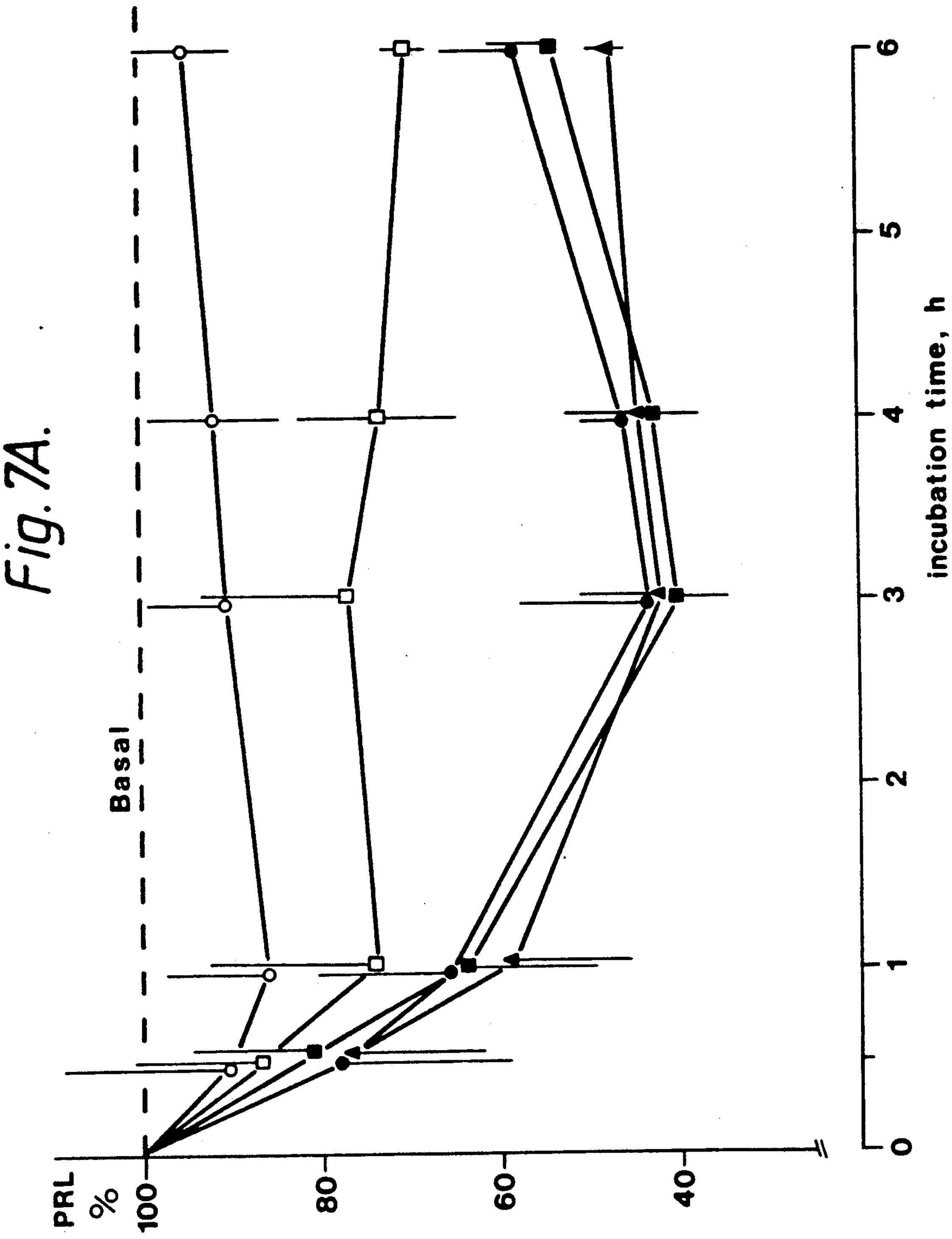
FIGS. 7A and B depict the PRL inhibiting activity of GAP.

The anterior pituitary cell culture from female Sprague-Dawley rats was prepared as described in Example 6. In FIG. 7A the indicated concentrations of GAP (open circles, $10^{-11}$M; open squares, $3\times10^{-11}$M; closed circles $10^{-10}$M; open squares, triangle $10^{-8}$M) were incubated with $5\times10^{5}$ cells/ml medium in 24-well culture plates for the indicated time. Media were assayed for PRL and values were expressed in terms of rPRL-RP-2 reference protein (National Pituitary and Hormone Program). The points are means ± standard deviation of four parallel culture wells of which duplicate samples were assayed by RIA. Basal levels were determined from eight parallel wells. The curves shown represent data obtained in three to five independent cell cultures.

Figure 7B:
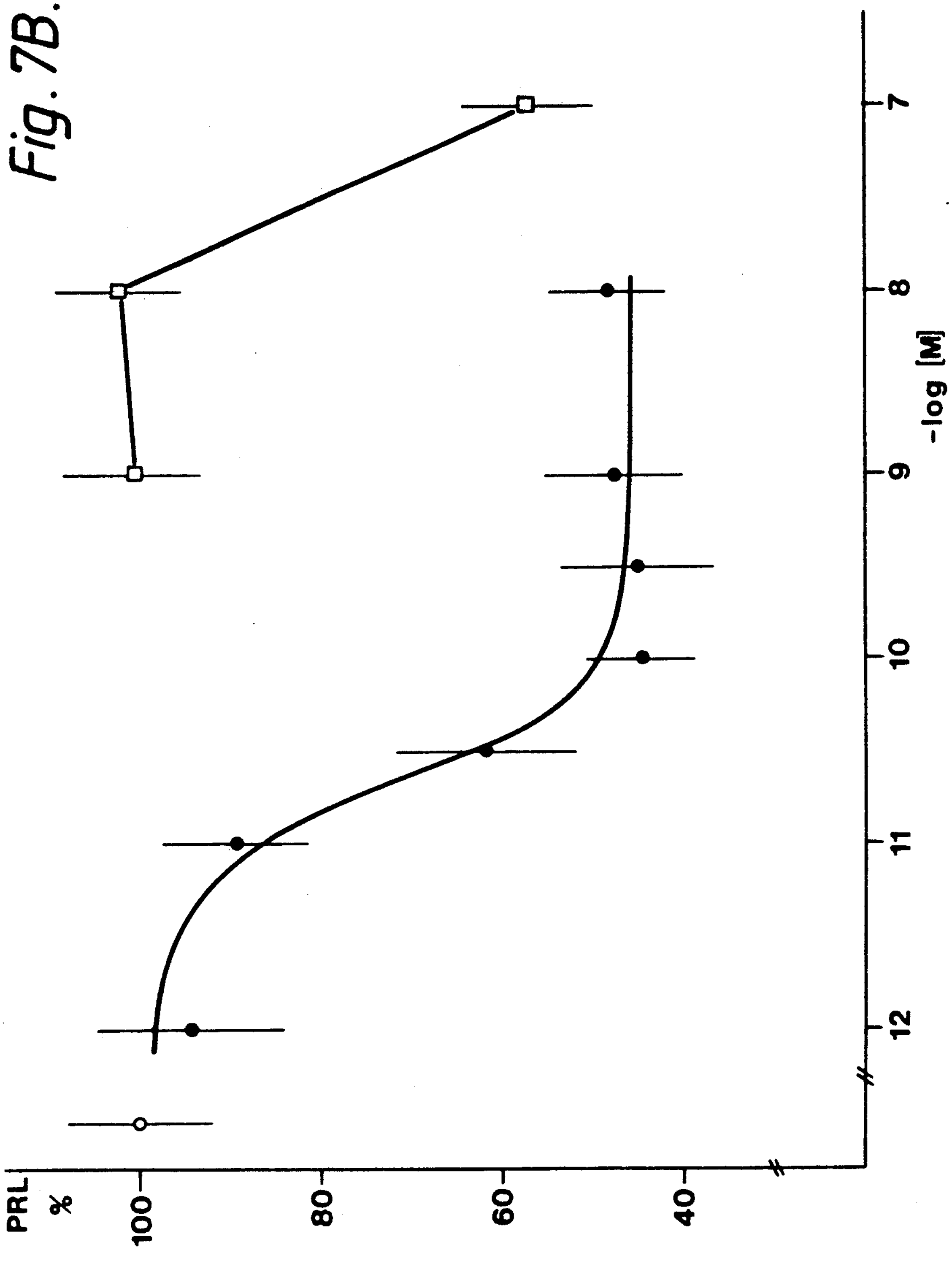

FIG. 7B depicts PRL secretion from the rat pituitary cells in the presence of increasing concentrations of GAP (closed circle) and dopamine (square). Control value without additions is the open circle. PRL secretion is expressed as a percent of uninhibited basal levels.

GAP exerted a significant inhibitory effect on the secretion of prolactin from pituitary lactotrophs. This effect was dose- and time-dependent, as shown in FIG. 7, with a maximal inhibition to 45-50 percent of the basal value. This inhibitory action of the peptide could be observed at very low concentrations. The magnitude of the inhibitory action of GAP on PRL secretion was comparable to that of dopamine (FIG. 7B). The two compounds did not act synergistically at lower concentrations. Thyrotropin releasing hormone (TRH), which stimulates the release of prolactin, caused a significant shift in the dose required for prolactin inhibition. In the presence of $10^{-7}$M TRH, higher does of GAP were required for maximal inhibition.

Increasing concentrations of GAP caused an increasing LH and FSH secretory response from rat anterior pituitary cells (Table 1). The maximum stimulation of the release of both gonadotropins was less than that induced by GnRH. Similar to GnRH, GAP stimulated both LH and FSH release. Half-maximal stimulation of LH release by GAP occurred at somewhat higher concentrations than by GnRH ($2\times10^{-9}$M for GAP vs. $8\times10^{-10}$M for GnRH). The two peptides, when applied together, did not show additive or synergistic characteristics but caused the same response as obtained with GnRH alone. However, GAP stimulated FSH secretion at approximately the same concentrations as GnRH with $ED_{50}$ values of the order of $5\times10^{-10}$M. The combination of GAP and GnRH did not result in significant additive activity.

It should be noted that the effective concentration range for the prolactin release inhibiting effect is lower than the corresponding gonadotropin release, suggesting that receptors which mediate the former action have a higher affinity for the peptide than receptors on gonadotrophs. Since lactotrophs are more abundant in the anterior pituitary than gonadotrophs, it is likely that the majority of the peptide molecules is normally bound to lactotrophs. Therefore, prolactin inhibition seems to be the primary action of CTP which can therefore be appropriately termed PIF. As a result, CTP species such as GAP are useful in treating diseases dependent upon prolactin and in modulating menses.

Examples of diseases dependent upon prolactin include hypogonadism in males and amenorrhea in females which are dependent upon hyperprolactinemia, as well as prolactin dependent tumors, especially mammary neoplasm. Potency in males and normal menstrual cycles in females are restored by administration of therapeutically effective doses of CTP species in pharmaceutically acceptable carriers. Suitable carriers are described above. Doses will be titered to the delivery mode and condition of the patient. However, in general a dose is sufficient which is effective to reduce plasma prolactin concentrations levels to basal levels, about from 5 to 25 ng/ml, as determined by conventional immunoassay in bromocriptive therapy (S. Sander et al., 1984, "J. Clinical Endocrinology and Metabolism" 59(5): 941-948: S. Winters et al., 1984, "Clinical Endocrinology" 21: 257-263; and A. Klibanski et al., 1984, "J. Clinical Endocrinology and Metabolism" 58(6): 1141-1147).

CTP compositions also are useful for veterinary purposes, primarily in rapidly restoring menses in postpartum animals and in modulating lactation. Lactation modulation for economically significant purposes generally means reducing the plasma levels of CTP in order to derepress PRL synthesis and release from the pituitary. This is best accomplished by immunizing dairy animals such as cattle against CTP by the administration of immunogenic CTP conjugates, e.g. the bacterial protein-CTP fusions described above or the BSA-CTP fragment conjugate described in Example 4. While it is possible to administer anti-CTP for passive immunization against CTP, for economic reasons it is preferable to actively autoimmunize the animal. Animal CTP is identified by probing genomic libraries from the species in question with a $^{32}$p-labelled 1500bp cDNA fragment of Example 2 to identity the CTP precursor DNA for the species of interest, sequencing the animal gene, and thereafter expressing it in recombinant culture or synthesizing it (or a core fragment thereof) by in vitro methods. Alternatively, antibodies raised against human CTP which cross-react with the CTP of the immunized species are useful.

We claim:

1. A method for synthesizing a polypeptide selected from the group of CTP and a fusion of CTP with another polypeptide, comprising:

(a) transforming a host cell with a vector known to encode the polypeptide;

(b) culturing the cell whereby the polypeptide is expressed; and (c) recovering CTP from the host cell culture or from the fusion of CTP with the second polypeptide.

2. The method of claim 1 wherein the fusion is with a microbial polypeptide bound to the N-terminus of CTP, or the tripeptide lys-lys-ile bound to the C-terminus of CTP.

3. The method of claim 2 wherein the microbial polypeptide is a bacterial signal operably linked to CTP.

4. The method of claim 7 wherein the fusion is with LHRH.

5. The method of claim 1 wherein the host cell is a yeast or bacterial cell.

6. The method of claim 1 wherein the polypeptide fused to CTP is free of proLHRH and LHRH.

7. The method of claim 1 wherein the synthesized polypeptide is CTP.

8. DNA encoding a polypeptide including a CTP amino acid sequence free of proLHRH, provided that the DNA is free of at least one intron when it encodes the polypeptide Met Lys Pro Ile Gln Lys Leu Leu Ala Gly Leu Ile Leu Leu Thr Ser Cys Val Glue Gly Cys Ser Ser Gln His Trp Ser Tyr Gly Leu Arg Pro Gly Gly Lys Arg Asp Ala Glu Asn Leu Ile Asp Ser Phe Gln Glu Ile Val Lys Glu Val Gly Gln Leu Ala Glu Thr Gln Arg Phe Glu Cy Thr Thr His Gln Pro Arg Ser Pro Leu Arg Asp Leu Lys Gly Ala Leu Glu Ser Leu Ile Glu Glu Glu Thr Gly Gln Lys Lys Ile.

9. DNA encoding a polypeptide including a CTP amino acid sequence free of proLHARH, provided that the DNA is extrachromosomal when it encodes the polypeptide Met Lys Pro Ile Gln Lys Leu Leu Ala Gly Leu Ile Leu Leu Thr Ser Cys Vel Glu Gly Cys Ser Ser Gln His Trp Ser Tyr Gly Leu Arg Pro Gly Gly Lys Arg Asp Ala Glu Asn Leu Ile Asp Ser Phe Gln Glu Ile Val Lys Glu Val Gly Gln Leu Ala Glu Thr Gln Arg Phe Glu Cys Thr Thr His Gln Pro Arg Ser Pro Leu Arg Asp Leu Lys Gly Ala Leu Glu Ser Leu Ile Glu Glu Glu Thr Gly Gln Lys Lys Ile.

10. The DNA of claim 9 which is operably ligated into a replicable vector.

11. A host cell transformed with the vector of claim 10.

* * * * *